United States Patent [19]

Matthes et al.

[11] Patent Number: 5,153,180

[45] Date of Patent: * Oct. 6, 1992

[54] FLUORINATED NUCLEOSIDES AND PROCESS FOR TREATING RETROVIRUS INFECTIONS THEREWITH

[76] Inventors: Eckart Matthes, Karower Chausee 129, 1115 Berlin; Christine Lehmann, Walter-Friedrich Str. 5, 1055 Berlin; Dieter Scholz, Heinrich-Roller Str. 16, 1055 Berlin; Martin von Janta-Lipinski, Pradelstr. 6, 1100 Berlin; Klaus Gaertner, Karower Chaussee 157, 1115 Berlin; Peter Langen, Karower Chaussee 219, 1115 Berlin; Hans-Alfred Rosenthal, Märkisches Ufer 14, 1020 Berlin, all of Fed. Rep. of Germany

[ * ] Notice: The portion of the term of this patent subsequent to Oct. 16, 2007 has been disclaimed.

[21] Appl. No.: 566,486

[22] Filed: Aug. 13, 1990

Related U.S. Application Data

[63] Continuation of Ser. No. 223,677, Jul. 15, 1988, Pat. No. 4,963,662, which is a continuation of Ser. No. 65,952, Jun. 24, 1987, abandoned.

[51] Int. Cl.$^5$ .............................................. A61K 31/70
[52] U.S. Cl. ................................... 514/50; 514/51
[58] Field of Search ............... 514/45, 46, 47, 48, 514/49, 50, 51; 536/23, 24, 26, 27, 29

[56] References Cited

U.S. PATENT DOCUMENTS 3,775,397 11/1973 Etzold et al. ........................ 536/23
4,963,662 10/1990 Matthes et al. ..................... 536/23

OTHER PUBLICATIONS

The Journal of Biological Chemistry, vol. 262, No. 5, Feb. 15, 1989 pp.2187–2189.

Primary Examiner—John W. Rollins
Attorney, Agent, or Firm—Schweitzer Cornman & Gross

[57] ABSTRACT

A process for treating AIDS, which comprises administering to a patient in need therefor a pharmaceutical composition comprising a therapeutically effective amount of a compound having the formula

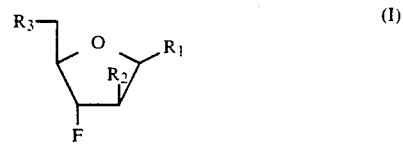

wherein:

$R_1$ is an adenine, cytosine, guanine, thymidine, uracil, 5-substituted uracil, 5-substituted cytosine derivative, 2-fluoroadenine, 2.6-diaminopurine, 2-aminopurine, 6-thioguanine, or 7-deazaadenine group;

$R_2$ is H, or a OH group;

$R_3$ is a OH, O-acyl, O-palmitoyl group or phosphates (as free acid, or its alkali, ammonium or alkyl ammonium salts), or any other precursor group for the hydroxyl group;

or a physiologically acceptable salt thereof. Furthermore, the present invention comprises the new compounds:

2′,3′-dideoxy-3′-fluoro-2-fluoroadenosine,
2′,3′-dideoxy-3′-fluoro-6-thioguanosine,
2′,3′-dideoxy-3′-fluoro-2,6-diaminopurineriboside,
2′,3′-dideoxy-3′-fluoro-2-aminopurineriboside,
2′,3′-dideoxy-3′-fluoro-5-aminomethyluridine,
2′,3′-dideoxy-3′-fluoro-5-azidomethyluridine, and
2′,3′-dideoxy-3′-fluoro-5-hydroxymethyluridine.

6 Claims, No Drawings

FLUORINATED NUCLEOSIDES AND PROCESS FOR TREATING RETROVIRUS INFECTIONS THEREWITH

This is a continuing application of U.S. Ser. No. 223,677, filed on Jul. 15, 1988, now U.S. Pat. No. 4,963,662, which is a continuing applicaton of U.S. Ser. No. 065,952, filed on Jun. 24, 1987, now abandoned.

FIELD OF THE INVENTION

The invention relates to fluorinated nucleosides and process for treating retrovirus infections, particularly of HIV type 1 and HIV 2 infections.

BACKGROUND OF THE INVENTION

Acquired immune deficiency syndrome (AIDS) has been known for only a few years as a new infectious disease in man. It is caused by the recently discovered retroviruses HIV 1 and HIV 2, which infect and destroy preferentially CD4+ T-helper lymphocytes. An immune deficiency is thus produced. This is manifested by the occurrence of opportunistic infections such as Kaposi's sarcoma and a so called AIDS-encephalopathy, which are generally progressive and inevitably lead to death. The development of AIDS and the preceding lymphadenopathy syndrome are dependent on active virus replication, which is closely related to the activity of the viral enzyme reverse transcriptase. Therefore effective and selective inhibitors of this viral polymerase raise the possibility of pre-preventing and slowing the progress of AIDS. The first clinically tested inhibitors of HIV reverse transcriptase, such as Suramin (Germanin TM) and HPA 23, have not reached the required level of efficiency and tolerability by the human body. Only 3'azido-2,3'-deoxythymidine ($N_3$-TdR) (German Federal Republic patent No. 3,608,606) has shown an unequivocal life extending effect in the case of AIDS patients with pneumocystis carinii pneumoniae, accompanied by improvements in clinical and neurological findings and a temporary restoration of certain immunological functions (Mitsuya et al., Nature 325, 773, 1987). However, the toxic side effects on the bone marrow required blood transfusions in about 50% of the patients treated with it. This indicates that inhibitors of HIV reverse transcriptase with higher selectivity and efficacy are required.

DESCRIPTION OF THE INVENTION

It was found that a mono- or polysubstituted pyrimidine- or purine nucleoside having the formula

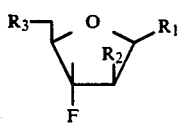

(I)

wherein:
R1 is an adenine, cytosine, guanine, thymidine, uracil, 5-substituted uracil, 5-substituted cytosine derivative, 2-fluoroadenine, 2,6-diaminopurine, 2-aminopurine, 6-thioguanine, or 7-deazaadenine group;
R2 is H, or a OH group;
R3 is a OH, O-acyl, O-palmitoyl group, or phosphates (as free acid, or its alkali, ammonium or alkyl ammonium salts), or any other precursor group for the hydroxyl group;
or a physiologically acceptable salt thereof, by itself or with a physiologically acceptable carrier, is effective against retrovirus infections, particularly infections with HIV types 1 and 2.

The invention comprises a process for treating AIDS, by administering to a patient in need therefore a pharmaceutical preparation containing as active ingredient a therapeutically effective amount of at least one compound of formula (I). The invention also comprises the following new compounds:
2',3'-dideoxy-3'-fluoro-2-fluoroadenosine,
2',3'-dideoxy-3'-fluoro-6-thioguanosine,
2',3'-dideoxy-3'-fluoro-2,6-diaminopurineriboside,
2',3'-dideoxy-3'-fluoro-2-aminopurineriboside,
2',3'-dideoxy-3'-fluoro-5-aminomethyluridine,
2',3'-dideoxy-3'-fluoro-5-azidomethyluridine, and
2',3'-dideoxy-3'-fluoro-5-hydroxymethyluridine.

Various compounds are referred herein by abbreviated names. The following tabulation provides an explanation of those abbreviations.

| abbreviation | complete name of compound |
|---|---|
| dTMP | 2',3'-dideoxythymidine-5'-monophosphate |
| FTdR | 2',3'-dideoxy-3'-fluorothymidine |
| FdTTP | 2'-3'-dideoxy-3'-fluorothymidine-5'-triphosphate |
| FddUrd | 2'-3'-dideoxy-3'-fluorouridine |
| FdUTP | 2'-3'-dideoxy-3'-fluorouridine-5'-triphosphate |
| FddFUrd | 2'-3'-dideoxy-3'-fluoro-5-fluorouridine |
| F5FdUTP | 2'-3'-dideoxy-3'-fluoro-5-fluorouridine-5'-triphosphate |
| FddBrUrd | 2'-3'-dideoxy-3'-fluoro-5-bromouridine |
| FddCNUrd | 2'-3'-dideoxy-3'-fluoro-5-cyanouridine |
| FddHMUrd | 2'-3'-dideoxy-3'-fluoro-5-hydroxymethyluridine |
| FddEtUrd | 2'-3'-dideoxy-3'-fluoro-5-ethyluridine |
| F5EtdUTP | 2'-3'-dideoxy-3'-fluoro-5-ethyluridine-5'-triphphosphate |
| FddCyt | 2'-3'-dideoxy-3'-fluorocytidine |
| FddMCyt | 2'-3'-dideoxy-3'-fluoromethylcytidine |
| FddGuo | 2'-3'-dideoxy-3'-fluoroguanosine |
| FdGTP | 2'-3'-dideoxy-3'-fluoroguanosine-5'-triphosphate |
| FddAdo | 2'-3'-dideoxy-3'-fluoroadenosine |
| FddDAPR | 2'-3'-dideoxy-3'-fluoro-2,6-diaminopurineriboside |
| FaraU | 3'-deoxy-3'-fluoroarabinosyluracil |
| FaraBrU | 3'-deoxy-3'-fluoroarabinosyl-5-bromouracil |
| FaraC | 3'-deoxy-3'-fluoroarabinosylcytosine |
| FdTMP | 2',3'-dideoxy-3'-fluorothymidine-5'-monophosphate |
| $N_3$-TdR | 3'-azido-2',3'-dideoxythymidine. |

The pyranose and the furanose forms are in equilibrium with each other. Accordingly, the furanose nomenclature was chosen for naming the arabinose compounds.

A. Inhibition of HIV Associated Reverse Transcriptase

At first the triphosphates of some compounds according to formula I were investigated for their ability to inhibit the polymerization of artificial templates (such as polyAoligodT and polyColigodG) catalyzed by HIV-associated reverse transcriptase (HIV-RT) according to the method described by A. D. Hoffman et al., Virology 147, 326, 1985. Table 1 demonstrates the concentrations required for a 50% inhibition of this viral enzyme ($ID_{50}$). FdTTP, FdUTP and FdGTP are among the strongest inhibitors found so far for HIV-RT. In comparison the $ID_{50}$ for 3'-azidothymidinetriphosphate was estimated under our conditions to be about 0.05 mM. Examination of the mode of action revealed, at least for FdTTP, a competitive type of inhibition rather than a DNA chain terminating incorporation.

In contrast to FdTTP, the corresponding 3'-chloro-2',3'-dideoxythymidine triphosphate was shown to be completely ineffective against HIV-associated reverse transcriptase at 1 mM μm, indicating that for a high degree of efficiency the nature of the 3'-substituent plays a critical role and cannot be simply replaced by any other group.

TABLE 1

Comparison of concentrations of 2',3'-dideoxy-3'-fluoronucleoside 5'-triphosphates required for a 50% inhibition ($ID_{50}$) of HIV-reverse transcriptase (HIV-RT) and the cellular DNA polymerases α, β

| | Compound | HIV-RT | $ID_{50}/um$ cellular polymerases | |
|---|---|---|---|---|
| | | | α | β |
| A | FdTTP | 0.05 | >200 | 2.2 |
| B | FdUTP | 0.07 | >200 | 3.0 |
| C | FdGTP | 0.05 | >200 | 1.8 |
| D | F5FdUTP | 0.45 | >200 | 15.0 |
| E | F5EtdUTP | 7.5 | 10 | 4.0 |

B. Effect on cellular DNA polymerases α and β

The strong inhibiting effect of 3'-fluoro-substituted deoxynucleotides against HIV-reverse transcriptase can be utilized therapeutically only if the cellular DNA polymerases, especially the DNA polymerase α which is required for the replication of the cellular DNA, remain substantially unaffected. As shown in Table 1, this could be confirmed for DNA polymerase α. A 50% inhibition of the cellular enzyme DNA polymerase has not been reached at 200 μm of the tested compounds demonstrating their high selectivity. The $ID_{50}$ values for the DNA polymerase β responsible for cellular DNA repair vary between 1,8–15 μm. Both enzymes cellular DNA polymerase α and β were purified from calf thymus and tested according to the method of E. Matthes et al., Biomed. Biochim. Acta 44. K63 (1985).

C. The intracellular phosphorylation of FTdR

The critical factor for 3'-fluoro-substituted deoxynucleosides to reach a high intracellular efficiency is their ability to be phosphorylated in situ in the infected cells. A lack of phosphorylation of 3'-modified deoxynucleosides may strongly reduce or even abolish the efficacy of a compound which proved to be highly effective in the HIV reverse transcriptase test, as in the case of 2',3'-dideoxythymidine. As shown in Table 2, FTdR is metabolized sufficiently to the triphosphate in all examined cell lines during a 24-hour incubation. The concentrations of FdTTP determined for uninfected human H9- and CEM-cells are in the same range as found for HTLV-III (HIV-1) infected H9 cells and LAV-II (HIV-2) infected CEM-cells, respectively, so that an AIDS virus infection of T-cells apparently does not change the ability of FTdR to be phosphorylated. By comparison, the phosphorylation of 50 μm $N_3$-TdR by HTLV-III$_B$-infected H9 cells to the triphosphate during a 24-hour incubation has been reported to reach only 0.9 pmoles/$10^6$ cells and to be accompanied by an extreme accumulation of the monophosphate of $N_3$-TdR (460 pmoles/$10^6$ cells), reflecting a strong inhibition of the dTMP-kinase (Furman et al., Proc. Natl. Acad. Sci. U.S.A. 83 8333 (1986)) and entailing considerable alterations of the deoxynucleoside triphosphate substrate pools (Furman et al., loc. cit.) which affect cellular DNA synthesis. FTdR does not have this adverse effect on the thymidylate kinase (see Table 2), so that the pronounced significant changes of the cellular pools of deoxynucleoside-triphosphates are not to be expected, although FTdR is distinctly better phosphorylated than $N_3$-TdR.

TABLE 2

Synthesis of nucleotides from 1/$um^3$ H-FTdR (tritium labeled) in cells of various species within 24 hours.

| | Cell line | mono-(FdTMP) | pmoles/$10^6$ cells phosphate di-(FdTDP) | tri-(FdTTP) |
|---|---|---|---|---|
| Human | MT4 | 9.9 | 1.6 | 5.6 |
| | CEM (LAV-II) | 6.1 | 0.5 | 2.8 |
| | H9 (HTLV-III$_B$) | 3.3 | 0.3 | 1.4 |
| Rat | NRK-49F | 3.5 | 3.7 | 13.2 |
| Mouse | 3T3 | 0.38 | 2.2 | 16.3 |

D. Resistance of 3'-fluoro-substituted pyrimidine-nucleoside analogs against phosphorolytic cleavage Some thymidine antimetabolites, such as 5-iododeoxyuridine, 5-bromodeoxyuridine and 5-bromovinyldeoxyuridine will be cleaved to a large extent by human thymidine-phosphorylase to inactive pyrimidine bases and sugar phosphates. This proved to be a most limiting factor with respect to their systemic in vivo applicability. Therefore FTdR, FddBrUrd and FddFUrd were investigated for their ability to be cleaved by thymidine-phosphorylase from human spleen. We have found that these compounds at 1 mM were cleaved within 3 hours only to an extent of 3–8% and can be considered as being resistant to this enzyme in comparison to thymidine (90% cleavage in 2 hours).

E. Inhibition of the cytopathic effect of HIV on MT-4 cells by 3'-fluoro-substituted deoxynucleosides Under in vitro conditions immortalized T-lymphocytes can be killed within few days by the cytopathic effect of HIV. We determined the actual efficacy of 3'-fluoro-substituted deoxynucleosides in protecting a T-cell-line against the cytopathic effect of HIV. For this purpose about 20,000 MT-4 cells (Harada et al. Science 229, 563 (1985)) were infected with HIV (titer: 0.04 m.o.i.) and incubated in the presence or absence of varying concentrations of compounds according to formula I, with 10% fetal calf serum (FCS) in 200 μl RPMI medium. After 6 days of incubation the viable cells were counted that were excluded from trypan blue staining.

Table 3 summarizes the results given as concentrations required for a 50% protection of the cells against the cytopathic effect of HIV ($ED_{50}$) and as a concentrations producing a 50% inhibition of cell proliferation ($CD_{50}$). The following compounds proved to be most effective and selective: FTdR FddUrd, FddBrUrd, FddDAPR and FddGuo. For FTdR the $ED_{50}$ was 0.003 μm and in a direct comparison for $N_3$-TdR this value was estimated to be 0.016 μm, indicating a 5 times higher antiviral activity of FTdR against $N_3$-TdR.

TABLE 3

Comparative potency and selectivity of 2',3'-dideoxy-3'-fluoronucleoides as inhibitors of HIV-replication in MT-4 cells

| Compound | 50% antiviral dose ($ED_{50}$)/um | 50% cytotoxic dose ($CD_{50}$)/um |
|---|---|---|
| FTdR | 0.003 | 1.1 |
| FddUrd | 0.275 | 75 |

TABLE 3-continued

Comparative potency and selectivity of 2',3'-dideoxy-3'-fluoro-nucleoides as inhibitors of HIV-replication in MT-4 cells

| Compound | 50% antiviral dose (ED$_{50}$)/um | 50% cytotoxic dose (CD$_{50}$)/um |
|---|---|---|
| FddFUrd | not detectable | >200 |
| FddBrUrd | 5 | 190 |
| FddCNUrd | not detectable | >500 |
| FddHMUrd | >500 | >500 |
| FddEtUrd | >500 | >500 |
| FddCyt | 25 | 62 |
| FddMCyt | 125 | 125 |
| FddGuo | 5 | 250 |
| FddAdo | >100 | 75 |
| FddDAPR | 6 | 480 |
| FaraU | >500 | >500 |
| FaraBrU | >100 | >100 |
| FaraC | >100 | >100 |

The combined inhibitory effect of a 3'-fluoro-substituted pyrimidine nucleoside (FTdR, FddUrd) and a 3'fluoro-substituted purine nucleoside (FddGuo, FddDAPR) on HIV induced cytopathic effect on MT-4 cells was examined and analyzed by the isobologram method [M. Baba et al. Antimicrob. Agents Chemother. 25. 515 (1984)]. The calculated fractional inhibitory concentrations (FIC) of the compounds combined (e.g. FIC$_{FTdR}$+FIC$_{FddGuo}$, or FIC$_{FddUrd}$+FIC$_{FddDAPR}$) provided a minimum FIC index between 0.5 and 1.0 indicating an additive to subsynergistic effect for these combinations, which do not reduce the viability of the MT-4 cells.

The foregoing data unequivocally establish in vitro the AIDS virus-inhibiting effect of the compounds of formula (I). However, in view of the current limitations on testing possibilities no in vivo dosage ranging could be carried out as yet. The term "therapeutically effective dose" as used in the specification and claims, means a dose of a pharmaceutical preparation containing an active ingredient a compound of formula (I), in an amount effective to bring about a therapeutic benefit, but without an undue toxic effect. The therapeutically effective dosage level can be established in each given case by routine experimentation. Some guidelines are provided by the data in Table 3 and by the following experiments.

F. Cytotoxicity of FTdR and FddUrd in Human Cell Cultures

Originally FTdR was developed as a cytostatic agent (P. Langen et al., Acta biol. med. Germ. 23, 759, 1969; and U.S. Pat. No. 3,775,397) and, therefore, its cytostatic efficacy has been examined in extensive prior studies. The examinations and tests conducted by the NCI program in the USA against 9 different animal tumors concluded that FTdR has only a weak cytostatic effect. Ehrlich-mouse-ascites-carcinoma cells (EMAC) represents an exception to that finding, and this is probably connected to its high capability of phosphorylation of FTdR, which is 10 times higher than in human cells. The fast reversibility of the cytostatic effects on EMAC cells was regarded as a special property of this compound (P. Langen et al., Europ. J. Cancer. 14. 349, 1978). The antiproliferative effect of FTdR and FddUrd, and in comparison thereto of N$_3$-TdR were tested on human cell lines with regard to a possible use in humans. Table 4 shows on the basis of the available CD$_{50}$ values that the cytostatic effects of FTdR and N$_3$-TdR vary considerably between different cell lines. When FTdR is compared to N$_3$-TdR. The effects are very similar, however somewhat lower in each case for N$_3$-TdR than for FTdR. In contrast, FddUrd does not show any substantial antiproliferative effect.

TABLE 4

Inhibition of proliferation of human cell-lines by FTdR and FddUrd in comparison to N$_3$-TdR

| Cells | Deviation | N$_3$-TdR | FTdR | FddUrd |
|---|---|---|---|---|
| K-562 | acute myeloic leukemia | 50 | 45 | >1.000 |
| REH | acute lymphatic leukemia | 220 | 160 | >9,000 |
| K-37 | immortalized T-cells | 500 | 260 | >1,000 |
| H9 | immortalized T-cells | 800 | 1000 | >2,500 |

CD$_{50}$: inhibitory dose required to reduce the cell number by 50%

G. Effects of FTdR on Mice Infected with Rauscher Murine Leukemia Virus (RLV)

At the present time there is no appropriate animal model available for testing anti AIDS-drugs. Therefore we examined the toxicity and antiretroviral activity of FTdR in mice infected with Rauscher murine leukemia virus. Different doses of FTdR were applied to BalB/c Han strain of mice in plain water for 20 days beginning 2-8 hours after RLV infection. Such a continuous application of FTdR at 69.0 mg/kg/day was able to prevent the development of a leukemia induced normally by this retrovirus within 3 weeks. As shown in Table 5 line F this concentration completely suppresses the appearance of splenomegaly as well as of RLV-associated reverse transcriptase activity in the serum. However toxic side effects are associated with this concentration range as demonstrated by hematological parameters (Table 5, EF). FTdR applied at a 10-fold lower concentration (6.5 mg/kg/day) failed to produce signs of anemia and depression of white cell counts but, nevertheless, it seems to be completely active in suppressing splenomegaly and viremia, as estimated by reverse transcriptase activity, see Table 5, lines C and D. A further reduction of the oral FTdR dose to 1.8 mg/kg/day, given for 24 days established that still more than 70% of serum reverse transcriptase activity and more than 50% suppression of splenomegaly took place. A direct investigation of the inhibitory activity of the triphosphate of FTdR (FdTTP) on the RLV-associated reverse transcriptase has shown that the concentrations required for a 50% inhibition of this enzyme (ID$_{50}$) is 0.5 μm, i.e., this enzyme is 10 times less sensitive to the inhibitor than the HIV-associated reverse transcriptase (ID$_{50}$=0.05 μm). These results, in addition to the very effective phosphorylation of FTdR by human cells, let us assume that doses of FTdR that are several times lower than are required for a complete suppression for RLV infection in mice (6.5 mg/kg/d), could be sufficient for the treatment of AIDS.

These results show clearly that FTdR is able to protect mice even 2-8 hours after an infection with a retrovirus (RLV), and an ability of the compounds of formula (I) even to prevent AIDS virus infection.

TABLE 5

Effects of continuous application of 6.5 or 69.0 mg/kg/day FTdR administered in the drinking water for 20 days on toxicity and development of RLV induced leukemia

|  |  | RLV | No. of mice | changes of body weight (%) | Hemoglobin (mMoles/l) | White blood cell count (per mL) | mean spleen weight (mg) | Reverse transcriptas serum (%)* |
|---|---|---|---|---|---|---|---|---|
| Control | A | − | 7 | +5 | 10.6 | 5740 | 101 | — |
|  | B | + | 10 | +10 | 7.2 | 4970 | 983 | 100 |
| FTdR | C | − | 5 | +1 | 8.9 | 5240 | 125 | — |
| 6.5 mg/kg/day | D | + | 10 | 0 | 8.1 | 4510 | 192 | 0 |
| FTdR | E | − | 5 | −12 | 4.3 | 1027 | 72 | — |
| 69.0 mg/kg/day | F | + | 10 | −10 | 5.1 | 733 | 86 | 0 |

Female BALb/c mice (20 gm) were infected with RLV. The oral RT treatment was started 2-3 hours later at the doses indicated. Results are given as mean values of each group.
*12 hours before estimation of RT activity the treatment was discontinued. 1 ml of the serum of 6 animals was used for RT-assay. 100% activity in this experiment means 66000 dpm.

The advantages of FTdR are summarized below:
5-fold the efficacy in comparison to $N_3$-TdR in cellular test;
better phosphorylation than $N_3$-TdR in human cell lines;
resistance against TdR-hosphorylase;
lower effects than $N_3$-TdR on TMP-kinase and also on the dNTP-substrate pools; and
tolerable and, especially reversible cellular toxicity.
Other effective compounds for use in accordance with the present invention, include:
2',3'-dideoxy-3'-fluoro-2-fluoroadenosine;
2',3'-dideoxy-3'-fluoro-6-thioguanosine;
2',3'-dideoxy-3'-fluoro-2-aminopurineriboside;
3'-deoxy-3'-fluoroarabinosyladenine;
3'-deoxy-3'-fluoroarabinosylthymidine;
2',3'-dideoxy-3'-fluoro-5-fluorocytidine;
2',3'-dideoxy-3'-fluoro-5-formylcytidine;
2',3'-dideoxy-3'-fluoro-5-aminouridine; and
2',3'-dideoxy-3'-fluoro-5-azidouridine.
2',3'-dideoxy-3'-fluoro-5-chlorouridine The invention also includes a method for the treatment or prophylaxis of AIDS in a human patient, which comprises administration of an agent containing a therapeutically effective amount of one or more of the compounds of formula (I) or a physiologically acceptable salt thereof to the patient, to produce an ameliorating effect of the AIDS symptom. The agent to be administered in accordance with the present invention contains one or more active substances of formula (I), together with one or more physiologically acceptable carriers, together with optional other therapeutically active ingredients. The agents are produced as a unit dose or multiples thereof. Each carrier that is used must be tolerable by the human patients, compatible with the other ingredients, and should not be harmful to patients.

The drugs of the present invention include all of those dosage forms which can be administered orally, rectally, nasally, topically, vaginally, or parenterally (including subcutaneously, intramuscularly, intravenously and intradermally). One or more active ingredients in accordance with formula (I) are contacted with the carrier which itself may also comprise one or more components and, if required, are then brought to a required galenic shape or form.

Drugs in accordance with the present invention for oral administration can be in the form of, tablets, capsules, powder, or granules which contain a predetermined amount of the active ingredient of formula (I). A solution or suspension can also be employed. Optionally, taste masking agents or the like can be added.

Drugs for rectal administration can be in the form of suppositories in a suitable base.

Drugs for vaginal administration can be in the form of suppositories, pessaries, tampons, creams, gels, pastes, foams, or spray products.

Parenteral administration can be accomplished in a unit dose of the active ingredient of formula (I), or in a multiple dose thereof, and can be stored, e.g., in ampoules, vials, or in freeze dried condition. Freshly prepared injectable solutions and suspensions can be also made from sterile powders, granulates and tablets. This can be achieved, for example, by dissolving the active ingredient of formula (I) in physiological salt solution, in glucose or in other media that are suitable for intravenous injection or infusion. For the treatment of AIDS patients suitably a 3% solution is prepared of the required amount of e.g. FTdR in a physiological salt solution. This is sterilized and within an hour of preparation is administered to the patient by intravenous infusion. The infusion is repeated every 4-8 hours and is continued for at least 8-10 days.

Esters and salts of the compounds of formula (I) can be conveniently prepared in a manner known per se, starting from a compound, for example, of formula (I) wherein $R_3$ in the 3'-fluorinated nucleoside can be a protected hydroxyl group, e.g., an ester group such as acetoxy, or an ether group, such as a trialkylsyliloxy, or triphenylmethoxy group. Such groups can be converted without transesterification into alternative ester groups, such as by hydrolysis, into the hydroxyl group.

The 3'-fluorinated nucleosides can be converted to a physiologically acceptable phosphate, or another ester by reaction with a phosphorylating agent, such as $POCL_3$, or a suitable esterifying agent, such as an acidhalogenide, or -anhydride [M. Yoshikawa et al., Tetrahedron Letters, 5065-68 (1967); D. E. Hoard et al., J. Am. Chem. Soc. 87, 1785-1788 (1965)]. The compounds of formula (I) can be converted with phosphate groups, in a manner known per se, into their physiologically acceptable salts, such as by treatment with a suitable base.

Preferred esters of the compounds in accordance with formula (I) include carbonic acid esters in which the non-carboxy part of the ester group comprises a straight-chain, or branched-chain alkyl, alkoxyalkyl (e.g. methoxymethyl), aralkyl (e.g. benzyl), aryl (e.g. unsubstituted phenyl, or substituted with halogen, $C_{1-4}$ alkyl, or $C_{1-4}$ alkoxy), mono-, di-, and triphosphate esters, and sulfonate esters, such as alkyl- or aralkylsulfonyloxy (e.g. methanesulfonyloxy, or p-toluenesulfonyloxy.

The following examples provide a further illustration of the present invention the full scope of which is defined by the claims. Any reference to a "compound of the invention" is meant to refer to a compound defined by formula (I).

EXAMPLE 1

Injection Solution

The required amount of a 3% solution is prepared from FTdR and physiological salt solution.

EXAMPLE 2

Uncoated or Coated Tablets

Powdered FTdR is formed into uncoated and coated tablets with one or more of the customary carriers, such as starch, talcum, magnesium stearate, potassium stearate, stearic acid, solid paraffin, cetyl alcohol, pectin, saccharose, arab gum, dextrin.

EXAMPLE 3

Preparation of 5-substituted 2',3'-dideoxy-3'-fluorouridines by cleavage of the 2',3'-anhydro bond (a)
1-(2',3'-Dideoxy-3-fluoro-$\beta$-D-ribofuranosyl)-5-ethyluracil A mixture of 2.30 g (mMoles) 2,3'-anhydro-1-(2-deoxy-O-acetyl-$\beta$-D-xylofuranosyl)-5-ethyluracil, 2.5 g aluminum trifluoride and 300 ml 1.4 dioxane, containing 0.5% hydrogen fluoride, was heated in a steel vessel to 110° C. for 1.5 hours. After cooling, 100 ml water and 20 g $CaCO_3$ were added to the reaction solution. The filtered solution was concentrated to a syrupy consistency, which was dissolved in 50 ml methanol saturated with ammonia at 0° C. and stored for 24 hours at room temperature. After expelling the solvent under vacuum the obtained oil was subjected to column chromatography on silica gel eluted with chloroform/methanol (9/1 vol/vol.). The title compound was obtained after solvent evaporation from the corresponding fractions as a solid substance. MP: 183°–184° C.; MS, m/z 258 ($M^+$).

(b)
5-Bromo-1-(2-3-dideoxy-3-fluoro-$\beta$-D-ribofuranosyl) uracil

A mixture of 5.31 g (10 mMoles) 2.3-anhydro-5-bromo-1-(2-deoxy-5-O-trityl-$\beta$-D-ribofuranosyl)uracil, 5.5 g aluminum trifluoride, and 400 ml 1.4-dioxane containing 0.5% hydrogen fluoride, was heated in a steel container to 110° C. for 1 hour. After cooling, the reaction solution was worked up as demonstrated in Example 3(a) to give a pale yellow crystalline material, MS: m/z 309 ($M^+$, $C_9H_{10}N_2O_4BrF$).

EXAMPLE 4

Preparation of 5-substituted 2',3'-dideoxy-3'-fluorouridines by radical bromination of the 5-methyl group in FTdR and subsequent nucleophilic substitution of the bromine (a) 5-(Bromomethyl)-1-(5-O-acetyl-3-deoxy-3-fluoro-$\beta$-D-ribofuranosyl) uracil 5'-O-acetyl-3'-fluorothymidine (2.88 g 10 mMoles) was heated in 250 ml 1.2-dichloroethane to complete dissolution under reflux. Thereafter 12 mMoles elementary bromine was introduced into the solution by a stream of nitrogen and the solution irradiated with a photolamp (500 W lamp made by NARVA). The reaction was terminated after 2-3 hours. The solvent was removed under vacuum under formation of a viscous oil. The latter contained the title compound in a purity sufficient for the subsequent reactions.

(b)
1-(2,3-Dideoxy-3-fluoro-$\beta$-D-ribofuranosyl)-5-hydroxymethyluracil

The bromination product obtained from 2.86 g (10 mMoles) 5'-O-acetyl-3'-fluorothymidine in step (a) was dissolved in 50 ml 1.4-dioxane, mixed with 30 ml saturated sodium bicarbonate solution, and stirred for 1 hour at room temperature. Subsequently, the reaction solution was extracted with 5×30 ml chloroform. The united chloroform extracts were dried over sodium sulfate filtered and concentrated under vacuum to give a syrupy oil. After the customary treatment with 50 ml methanol/ammonia (saturated at 0° C.) this product yielded the title compound, which was obtained in crystalline form from ethanol. M.P. 184° C.; MS: m/z 260 ($M^+$, $C_{10}H_{13}O_5N_2F$).

(c)
5-Aminomethyl-1-(2,3-dideoxy-3-fluoro-$\beta$-D-ribofuranosyl)uracil

The brominated product obtained from 2.86 g (10 mMoles) 5'-O-acetyl-3'-fluorothymidine in step (a) was dissolved in 50 ml 1,4-dioxane. This reaction solution was cooled at 0° C. and gaseous ammonia was bubbled through it. After 40 minutes of stirring in the ammonia atmosphere, the mixture was filtered to remove salts, and the filtrate was concentrated to dryness under reduced pressure. The crude product was purified by chromatography on a column of silica gel 60 (100 g) with 95:5 chloroform - methanol as the eluting solvent. Effluent fractions that were shown by means of a recording UV monitor to contain the desired product were combined and concentrated to dryness. The residue was titrated with 1:1 methanol - ethylacetate (5 ml) and the crystalline product was collected by filtration MS: m/z 259 ($M^+$, $C_{10}H_{14}N_3O_4F$).

(d)
5-Azidomethyl-1-(2,3-dideoxy-3-fluoro-$\beta$-D-ribofuranosyl)uracil

A suspension of the bromination product obtained from 2.86 g (10 mMoles) 5'-O-acetyl-3,-fluorothymidine, 3.25 g (50 mMoles) sodium azide and 100 ml of dry 1.4-dioxane was heated under gentle reflux for 3 hours. After cooling to room temperature the solution was filtered and concentrated under vacuum to a solid residue. Water (50 ml) and chloroform (30 ml) were added to the above residue, and, after removing of the organic layer the water solution was extracted successively with three 30 ml portions of chloroform. The combined chloroform phases were concentrated under reduced pressure to a brown residue. The O-acetyl group was removed by standard procedure with ammonia - methanol. The desired product was isolated by chromatography of the crude product on a column of silica gel 60 (150 g) with 95:5 chloroform - methanol as eluting solvent. Fractions that were shown by thin layer chromatography (TLC) to contain the desired product were combined and concentrated in vacuum to a pale yellow colored solid. MS: m/z 285 ($M^+$, $C_{10}H_{12}N_5O_4F$).

EXAMPLE 5

Preparation of 2',3'-dideoxy-3'-fluoro purine ribosides by fluorination of corresponding xylo derivatives with dialkylaminosulfur trifluoride 9-(2,3-Dideoxy-3-fluoro-β-D-ribofuranosyl)-2-fluoroadenine
(2',3'-dideoxy-3'-fluoro-2-fluoroadenosine)

10 mMoles 9-(5-O-acyl-2-deoxy-β-D-xylofuranosyl)-2-fluoroadenine was dissolved in 10 ml chloroform and added to a solution of 11 mMoles diethylaminosulfur trifluoride in 30 ml chloroform, which had been cooled to $-75°$ C. The reaction mixture was slowly heated to room temperature and added to 100 ml ice cold water. The organic phase was separated, washed with sodium bicarbonate and water and dried over sodium sulfate. After expelling the chloroform under vacuum a product was obtained, the O-acyl group of which was removed in a known manner. A column chromatographic separation on silica gel with chloroform (5% methanol) as eluent yielded the title compound as a solid substance MS: m/z 271 (M+, $C_{10}H_{11}O_2N_5F_2$).

EXAMPLE 6

Transglycosidation to obtain 2- or 2.6 substituted 2',3'-dideoxy-3'-fluoropurine ribosides 9-(2,3-Dideoxy-3-fluoro-β-D-ribofuranosyl)-2-fluoroadenine A mixture of 2.88 g (10 mMoles) 1-(5-O-acetyl-2,3-dideoxy-3-fluoro-β-D-ribofuranosyl) thymine, 4.6 g (30 mMoles) 2-fluoroadenine, 7.4 ml bistrimethylsilyl acetamide, and 250 ml acetonitrile was heated on reflux for 25 minutes. Subsequently, 6.5 ml (33 mMoles) trifluoromethanesulfonic acid trimethyl ester was added and the reaction mixture heated on reflux for further 8 hours. After removal of the solvent under vacuum the residue was suspended in 100 ml chloroform and neutralized with NaHCO3 solution. The organic phase was dried over sodium sulfate filtered and the chloroform removed under vacuum. The residue was separated by column chromatography on silica gel, eluting with chloroform (1 l of 5% n-hexane; 15 l of 2.5% n-hexane; 1 l of 1% n-hexane). The obtained mixture was deacetylated in a conventional manner by means of ammonia/methanol and was subjected to column chromatographic separation. Chloroform (1% methanol) was used as eluent. 0.51 g was isolated of the β anomer, the title compound. Further compound remained in the mixture with the α anomer.

EXAMPLE 7

Preparation of 5-substituted 2',3'-dideoxy-3'fluorocytidines from the corresponding uridine 1-(2,3-Dideoxy-3-fluoro-β-D-ribofuranosyl)-5-methylcytidine (2',3'-dideoxy-3'-fluoro-5-methylcytidine 1.5 (5.2 mMoles) 5'-O-acetyl-3'-fluorothymidine was dissolved in 25 ml pyridine and mixed with 760 mg (11 mMoles) triazole and 1.96 g (8 mMoles) β-chlorophenoxyphosphoric acid dichloride. The reaction mixture remained at room temperature for 5 days. Subsequently 30 ml dioxane in conc. ammonia (3:1 vol/vol) was added. The solution was concentrated under vacuum, the resulting residue was dissolved in water and charged into a 70 ml column of DOWEX 50 W×S, H+ form (packed with "DOWEX" ion exchange resin sold by DOW Chemical). The column was eluted first with 800 ml water and then with 600 ml 5% ammonia solution. 0.8 g. 2',3'-dideoxy-3'fluoro-5-methylcytosine was obtained as the hydrochloride from the corresponding fractions, containing UV-absorbing product, after expulsion of the solvent and crystallization from methanol (brought to pH 2 with HCl). Melting point 177° C. (decomposition), MS: m/z 243 (M+, $C_{10}H_{14}O_3N_3F$).

EXAMPLE 8

Preparation of 3'-deoxy-3'-fluoro-arabinosylcytosine from 3'-deoxy-3'-fluoroarabinosyl-1-(3'-deoxy-3'-fluoro-β-D-arabinosyl)cytosine A mixture of 2.45 g (10 mMoles) 3'-deoxy-3'-fluoroarabinosyluracil, 1.52 g (12 mMoles) triazole, 4 0 g (16 mMoles) p-chlorophenoxyphosphoric acid dichloride in 50 ml pyridine was treated as in Example 5.

After separation of the reaction mixture was separated on a column packed with DOWEX 50 W×8 (H+-form), 1.53 g of the title compound was obtained from methanol/HCl at pH 2 as hydrochloride, MS: m/z 246 (M+, $C_9H_{11}\ o_5N_2F$).

EXAMPLE 9

3'-Deoxy-3'-fluoro-5'-O-palmitoyl-thymidine

At 0° C., 1.2 equivalents of palmitoyl chloride are added to a solution of 3'-deoxy-3'-fluorothymidine in pyridine. The solution is warmed slowly to room temperature. As soon as a thin layer chromatographic control (CHCl3/methanol=95/5 on silica gel) shows a complete reaction, the solution is poured into ice water. The aqueous phase is decanted, the resulting oil is chromatographed on silica gel with chloroform eluent. The title compound is recovered from the suitable fractions by evaporation of the solvent. M.P. 65°–66° C. (cyclohexane).

EXAMPLE 10

Preparation of 5'-O-acetyl-3'-deoxy-3'-fluorothymidine 56 mMol acetanhydride is added at 0° C. to a solution of 50 mMol 3'-deoxy-3'-fluorothymidine in 50 ml pyridine. The reaction solution stands overnight at room temperature and is subsequently poured into ice water. The aqueous phase is decanted. The oily product is purified in a chromatographic column on silica gel with chloroform eluent. The fractions obtained from the product are isolated as a solid material which is recrystallized from ethanol. M.P.97°–98° C.

The esters of other 3'-fluorinated nucleosides are produced similarly as in Examples 9 or 10 from the corresponding acid chloride or -hydride.

EXAMPLE 11

Preparation of the 5'-monophosphate of 3'-deoxy-3'-fluorothymidine 1 mMol 3'-deoxy-3'-fluorothymidine is dissolved in 3 ml trimethylphosphate and the solution is cooled to $-3°$ C. 3 mMol phosphor oxychloride is added to this solution while stirring. The reaction solution is rested at $-3°$ C. for 24 hours. Then 5 ml water is added and the solution is neutralized with triethylamine. The reaction mixture is purified on a 2×35 mm column with DEA-Sephadex A-25 packing and eluted with pH 7–8 triethylammonium hydrogen carbonate with a linear gradient of 0-0.4M. The monophosphate is obtained as the triethylammonium salt from the corresponding fractions after driving out the buffer solution.

EXAMPLE 12

Preparation of the sodium salt of the 5'-monophosphate of 3'-deoxy-3'-fluorothymidine The nucleoside obtained in Example 11 is dissolved in a small volume of methanol and is reacted dropwise with 0.5 ml of a molar solution of sodium iodide in acetone. The resulting precipitate is centrifuged several times, each washed with 5 ml dry acetone and dried in vacuum over phosphorus pentoxide.

EXAMPLE 13

Hydrogen form of 3'-deoxy-3'-flourothymidine-5'-monophosphate

The hydrogen form of the monophosphate is prepared by dissolving the ammonium salt obtained in Example 11 in 4 ml water and passing it through a column packed with 3 ml DOWEX-50W×8 (H+-form) ion exchange resin.

EXAMPLE 14

Preparation of the 5'-triphosphate from 3'-deoxy-3'-fluorothymidine 0.1 mMol of the monophosphate prepared in accordance with Example 11 is changed into the corresponding pyridinium salt by passing it through DOWEX-50W×8 cation exchange resin (pyridinium form). By adding 2 equivalent tri-n-butylamine, the tributylammonium salt is obtained which is then further treated through repeated adding of dry pyridine and N,N-dimethylformamide and reduction of the solvent. 0.5 mMol 1,1'-carbonylbis(imidazole) is added to the solution of the anhydrous tributylammonium salt in 2 ml dimethylformamide. The progress of the reaction is controlled by thin film chromatography (cellulose: 6/3/1=isopropanol/conc. ammonia/water). After completion of the reaction 35 µl methanol is added and the reaction solution is rested for 15 minutes at room temperature. Next 0.5 mMol tributylammonium pyrophosphate (prepared from the pyridinium salt by adding 4 equivalent tributylamine) in 5 ml N,N-dimethlyformamide is added, and the mixture is rested for several hours at room temperature. After driving out the solvent the triphosphate is cleaned through a 2×35 cm DEAE-Sephadex A-25 column with pH 7-8 triethylammonium hydrogen carbonate buffer with a linear gradient of 0.05-0.6M.

EXAMPLE 15

Preparation of the 5'-diphosphate of 3'deoxy-3'-flourothymidine 0.3 mMol of the hydrogen form of the monophosphate obtained in Example 13, is dissolved in 5 ml water. 1.2 mMol morpholine is added and the solution is heated under reflux. During a 3 hour period a solution of 1.2 mMol dicyclohexylcarbodiimide in 4 ml tert-butanol is added. The reaction solution is held under reflux for 12 hours, cooled, filtered and the solvent is removed under vacuum. Ethanol is added and the solvent is again driven off. The procedure is repeated three times. The residue is dissolved in a small amount of methanol and the phosphormorpholinate precipitates by addition of ether. By reacting the precipitate four times, each time with 10 ml pyridine, and removal of the solvent under vacuum, the phosphomorpholinate is dried and finally dissolved in 5 ml pyridine. This solution is reacted with 2 mMol bis(tri-N-butyl- ammonium)-pyrophosphate and is held overnight at room temperature. Finally the solvent is removed under vacuum. The residue is dissolved in 70 ml water and charged on a 2×25 cm DEAE-Sephadex A-25 column, which was equilibrated with 0.05 mMol ammoniumbicarbonate. The phosphates are eluted with a linear gradient of 0.05-0.8 Mol of ammoniumbicarbonate. The corresponding fractions which contain the diphosphate nucleoside, are combined, as well as those which contain the triphosphate nucleoside. Each of the combined fractions are dried under vacuum, dissolved again in water, dried again, then dissolved in water and freeze-dried.

EXAMPLE 16

9-(2,3-Dideoxy-3-fluoro-β-D-ribofuranosyl)-6-thioguanosine

A mixture of 2.88 g (10 mMol) 1-(5-O-acetyl-2,3-dideoxy -3-fluoro-β-D-ribofuranosyl) thymine, 5.04 g (30 mMol) 6-thioguanine, 7.4 ml bistrimethylsilyl acetamide and 250 ml acetonitrile is heated at reflux for 40 minutes with stirring. Subsequently 6.5 ml (33 mMol) of trifluoromethanesulfonic acid trimethylsilylester is added and the reaction mixture is refluxed for 8 hours. The solvents are evaporated under vacuum, the syrupy residue is suspended in 100 ml of chloroform and neutralized with $NaHCO_3$ solution. The chloroform extract is filtered, dried with sodium sulfate and concentrated under vacuum to a small volume. The residue is chromatographed over a column of silica gel G 40 (35×2.5 cm). The column is washed successively with 500 ml each of 5% n-hexane-$CHCl_3$, 2.5% n-hexane-$CHCl_3$, 1% n-hexane-$CHCl_3$, and $CHCl_3$. The corresponding fractions that show containing the desired purine nucleoside as a mixture of the anomers, are combined and evaporated to dryness. The obtained protected nucleoside mixture is dissolved while stirring in a freshly prepared solution (about 50 ml/4 mequivalent of nucleoside) of 0.3N sodium methoxide. When thin layer chromatography indicates that the reaction is complete, an equivalent of water is added and the solution is neutralized by the addition of DOWEX 50 W×8 (pyridinium form) ion-exchange resin. The resin is filtered and the filtrate is evaporated to dryness. The residue is applied to a column of silica gel G 40 (35×2.5 cm) which is eluted with chloroform (1% methanol). Evaporation of the appropriate fractions leads to the isolation of the title compound (0.47 g). MS: m/z 285, (M+,$C_{10}H_{12}N_5O_2SF$).

EXAMPLE 17

2.6-Diamino-9-(2,3-dideoxy-3-fluoro-β-D-ribofuranosyl) purine

A mixture of 2.88 g (10 mMol) 1-(5-O-acetyl-2,3-dideoxy-3-fluoro-β-D-ribofuranosyl) thymine. 7.16 g (20 mMol) 2,6-bis-(aminobenzoyl) purine and 5 ml bistri- methylsilyl acetamide in 200 ml acetonitrile is heated at reflux for 35 minutes with stirring. Trifluoromethanesulfonic acid trimethylsilylester 6.5 ml (33 mMol) is added and the reaction mixture is refluxed for 10 hours. After the mixture is cooled, the solvent is removed under vacuum, and the residue is dissolved in chloroform, neutralized with $NaHCO_3$ and filtered free of insoluble materials. The filtrate is evaporated and the residue is chromatographed over a column of silica gel G 40 (35×2.5 cm) using CHCl$_3$ (1% n-hexane) as the eluent. The obtained protected nucleosides are a mixture of anomers. The protecting groups are removed by treatment with a solution of 0.3N sodium methoxide. The solution is neutralized by the addition of DOWEX 50 W×8 (pyridinium form) ion-exchange resin. The resin is filtered and the filtrate is evaporated to dryness. The residue is applied to a column of silica gel G 40 (35×2.5 cm) which is eluted with chloroform. The corresponding fractions are evaporated to give 0.23 g 2,6-diamino-9-(2,3-dideoxy-3-fluoro-β-D-ribofuranosyl) purine. MS: m/z 268, (M$^+$, C$_{10}$H$_{13}$N$_6$O$_2$F).

EXAMPLE 18

2-Amino-9-(2,3-dideoxy-3-fluoro-β-D-ribofuranosyl) purine

A solution of 2.88 g (10 mMol) 1-(5-O-acetyl-2,3-dideoxy -3-fluoro-β-D-ribofuranosyl) thymine. 7.17 g (30 mMol) 2-aminobenzoyl purine and 7.4 ml bistrimethylsilyl acetamide in 250 ml acetonitrile is heated at reflux for 30 minutes with stirring. Subsequently 6.5 ml (33 mMol) trifluormethanesulfonic acid trimethylsilylester is added and heating is continued for 7 hours. The solvent is removed under reduced pressure, the residue is dissolved in 100 ml chloroform and neutralized with a saturated solution of NaHCO$_3$. The organic layer is separated and the solvent is evaporated under vacuum. The residue is chromatographed over a column of silica gel G 40 (35×2.5 cm), using chloroform (1% n-hexane) as the eluent. The obtained mixture of the protected anomers of the purine nucleoside is dissolved in a freshly prepared solution of 0.3N sodium methoxide. When thin layer chromatography indicates that the reaction is complete in about 2-3 hours, water (10 ml) is added, and the solution is neutralized to pH6-7 by the addition of DOWEX 50 W×8 (pyridinium form) ion-exchange resin. The resin is filtered and washed with methanol and water, and the combined filtrates are evaporated to dryness. The residue is dissolved in water and repeatedly washed with CHCl$_3$ and Et$_2$O. The aqueous phase is then filtered and evaporated to dryness. Chromatography of the residue on a silica gel column using chloroform (1% methanol) as eluent leads, after evaporation of the appropriate fractions, to the isolation of 0.15 g of 2-amino-9-(2,3-dideoxy-3-fluoro-β-D-ribofuranosyl) purine. A substantial amount of the title compound remains in the mixture with the α-anomer. MS: m/z 253, (M$^-$, C$_{10}$H$_{12}$N$_5$O$_2$F).

We claim:

1. A method for treating HIV infection, which comprises administering to a patient in need therefore a pharmaceutical composition comprising a therapeutically effective amount of a compound having the formula

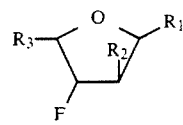

wherein
R$_1$ is a 5-substituted uracil group.
R$_2$ H, or a OH group; and
R$_3$ is a OH, O-acyl, O-palmitoyl group, or phosphates (as free acid, or its alkali, ammonium or alkyl ammonium salts), or any other precursor group for the hydroxyl group; or a physiologically acceptable salt thereof.

2. The method of claim 1, wherein the composition further comprises a pharmaceutically acceptable carrier.

3. The method of claim 2, wherein the composition further comprises a flavoring agent.

4. The method of claim 1, wherein the composition is in a dosage form suitable for administration by injection, infusion, oral ingestion, or anal application.

5. The method of claim 1, wherein the composition is in a dosage form of a coated or uncoated tablet, a capsule, powder, granule, suppository, in the form of a unit dose or a multiple thereof.

6. The method of claim 1, wherein said compound is one or more of:
2'-3'dideoxy-3'fluoro-5-bromouridine,
2'-3'dideoxy-3'fluoro-5-aminouridine,
2'-3'dideoxy-3'fluoro-5-azidouridine
2'-3'dideoxy-3'fluoro-5-flourouridine
2'-3'dideoxy-3'fluoro-5-aminomethyluridine,
2'-3'dideoxy-3'fluoro-5-azidomethyluridine
2'-3'dideoxy-3'fluoro-5-chlorouridine.

* * * * *

UNITED STATES PATENT AND TRADEMARK OFFICE
CERTIFICATE OF CORRECTION

PATENT NO. : 5,153,180
DATED : October 6, 1992
INVENTOR(S) : Eckart Matthes et al.

It is certified that error appears in the above-indentified patent and that said Letters Patent is hereby corrected as shown below:

Column 16, line 6,

In claim 1: line 2, change "therefore", to --therefor--;
change the formula to

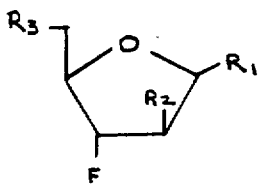

Column 16, lines 39-45,

In claim 6: in all 7 compounds, change "2'-3'dideoxy-3'fluoro..."
to --2',3'-dideoxy-3'-fluoro...--.

Signed and Sealed this

Second Day of November, 1993

Attest:

BRUCE LEHMAN

Attesting Officer

Commissioner of Patents and Trademarks